(12) United States Patent
Mizukami et al.

(10) Patent No.: US 8,163,471 B2
(45) Date of Patent: *Apr. 24, 2012

(54) REAGENT FOR SAMPLE ANALYSIS, KIT FOR SAMPLE ANALYSIS AND METHOD FOR SAMPLE ANALYSIS

(75) Inventors: Toshihiro Mizukami, Halstenbek (DE); Hiroki Takeshita, Kobe (JP); Tatsuya Narikawa, Kobe (JP)

(73) Assignee: Sysmex Corporation, Hyogo (JP)

( * ) Notice: Subject to any disclaimer, the term of this patent is extended or adjusted under 35 U.S.C. 154(b) by 168 days.

This patent is subject to a terminal disclaimer.

(21) Appl. No.: 11/806,904

(22) Filed: Jun. 5, 2007

(65) Prior Publication Data

US 2007/0287145 A1    Dec. 13, 2007

(30) Foreign Application Priority Data

Jun. 8, 2006    (JP) ................. 2006-159972

(51) Int. Cl.
*C12Q 1/00* (2006.01)
(52) U.S. Cl. ......................................... 435/4
(58) Field of Classification Search .............. 435/4
See application file for complete search history.

(56) References Cited

U.S. PATENT DOCUMENTS

| | | | |
|---|---|---|---|
| 5,316,814 A | 5/1994 | Sawada et al. | |
| 5,445,853 A | 8/1995 | Hayashi et al. | |
| 5,518,928 A * | 5/1996 | Cremins et al. | 436/10 |
| 5,631,165 A * | 5/1997 | Chupp et al. | 436/43 |
| 5,677,183 A | 10/1997 | Takarada et al. | |
| 6,004,536 A * | 12/1999 | Leung et al. | 424/9.6 |
| 6,168,844 B1 | 1/2001 | Takagishi et al. | |
| 6,664,110 B1 * | 12/2003 | Tsuji et al. | 436/63 |
| 7,101,678 B1 | 9/2006 | Montero-Julian et al. | |
| 7,332,295 B2 | 2/2008 | Valle | |
| 2007/0013906 A1 | 1/2007 | Kawate | |
| 2007/0254331 A1 | 11/2007 | Kawashima | |
| 2007/0287145 A1 | 12/2007 | Mizukami et al. | |

FOREIGN PATENT DOCUMENTS

| | | |
|---|---|---|
| EP | 0 353 393 A2 | 2/1990 |
| EP | 0895231 A2 * | 7/1998 |
| EP | 0 895 231 A2 | 2/1999 |
| EP | 0 919 008 A | 6/1999 |
| EP | 0353393 A2 * | 7/1999 |
| EP | 1 363 126 A1 | 11/2003 |
| JP | 10-339729 A | 12/1998 |
| JP | 2002-148261 * | 5/2002 |
| JP | 2002-148261 A | 5/2002 |
| JP | 2007-524771 A | 8/2007 |
| WO | 98/07061 A1 | 2/1998 |
| WO | 00/16103 A1 | 3/2000 |
| WO | 2005/085842 A2 | 9/2005 |

OTHER PUBLICATIONS

Aramendia, Pedro F. et al: "Temperature Dependence of Fluorescence and Photoisomerization in Symmetric Carbocyanines. Influence of Medium Viscosity and Molecular Structure" Journal of Physical Chemistry, vol. 98, No. 12, pp. 3165-3173, 1994.

Lepkowicz, Richard S. et al: "Femtosecond-to-nanosecond nonlinear spectroscopy of polymethine molecules" Journal of the Optical Society of America B: Optical Physics, vol. 22, No. 12, pp. 2664-2685, 2005.

Sims, P, J. et al: "Studies on the mechanism by which cyanine dyes measure membrane potential in red blood cells and phosphatidylcholine vesicles", Biochemistry, vol. 13, No. 16, Jul. 30, 1974, pp. 3315-3330.

* cited by examiner

*Primary Examiner* — Nizal Chandrakumar
(74) *Attorney, Agent, or Firm* — Sughrue Mion, PLLC

(57) ABSTRACT

A reagent for measuring basophils and/or nucleated red blood cells in a sample, which comprises at least one fluorescent dye defined in the formula (I) or (II) is disclosed. Also disclosed are a kit and method for measuring basophils and/or nucleated red blood cells.

4 Claims, 4 Drawing Sheets

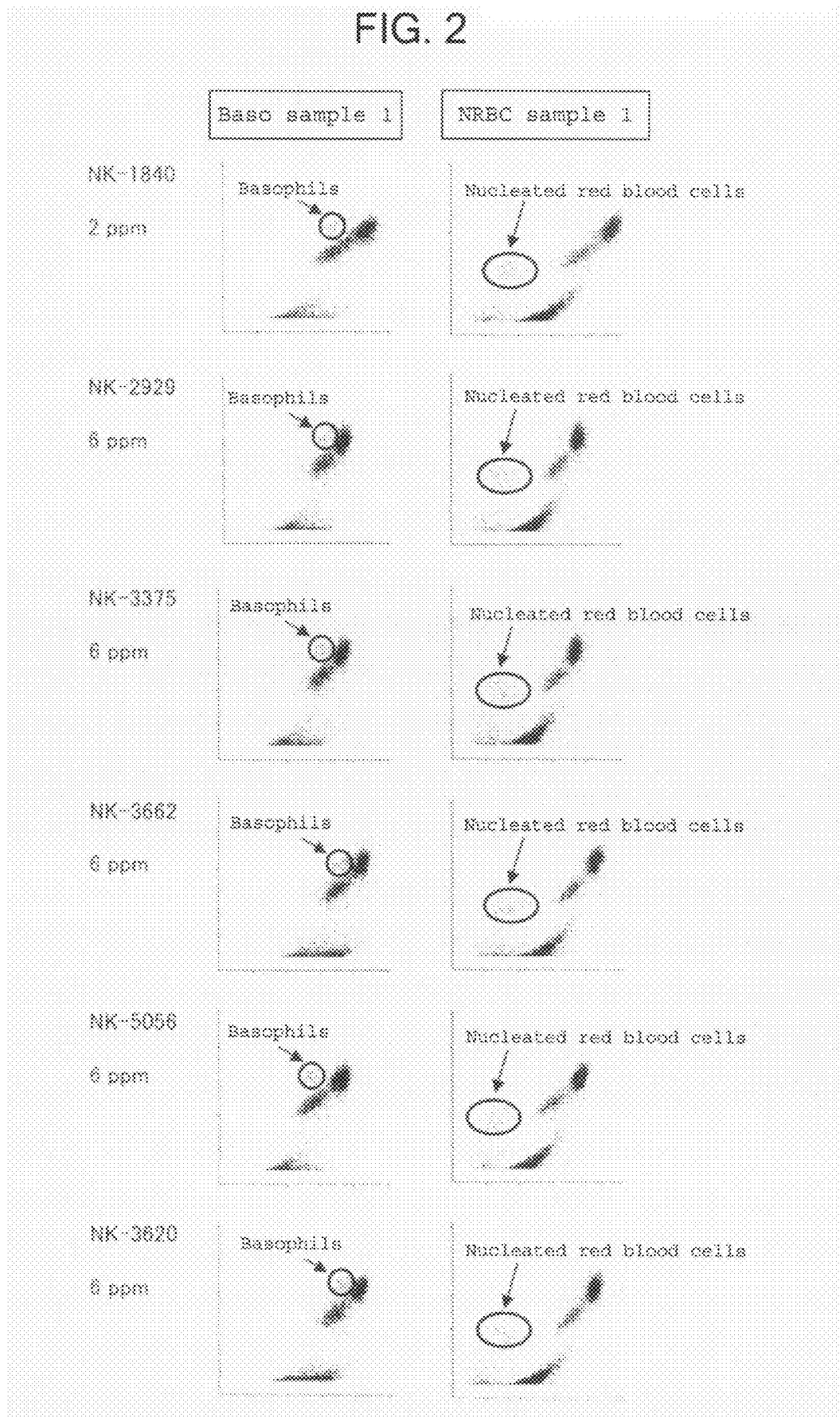

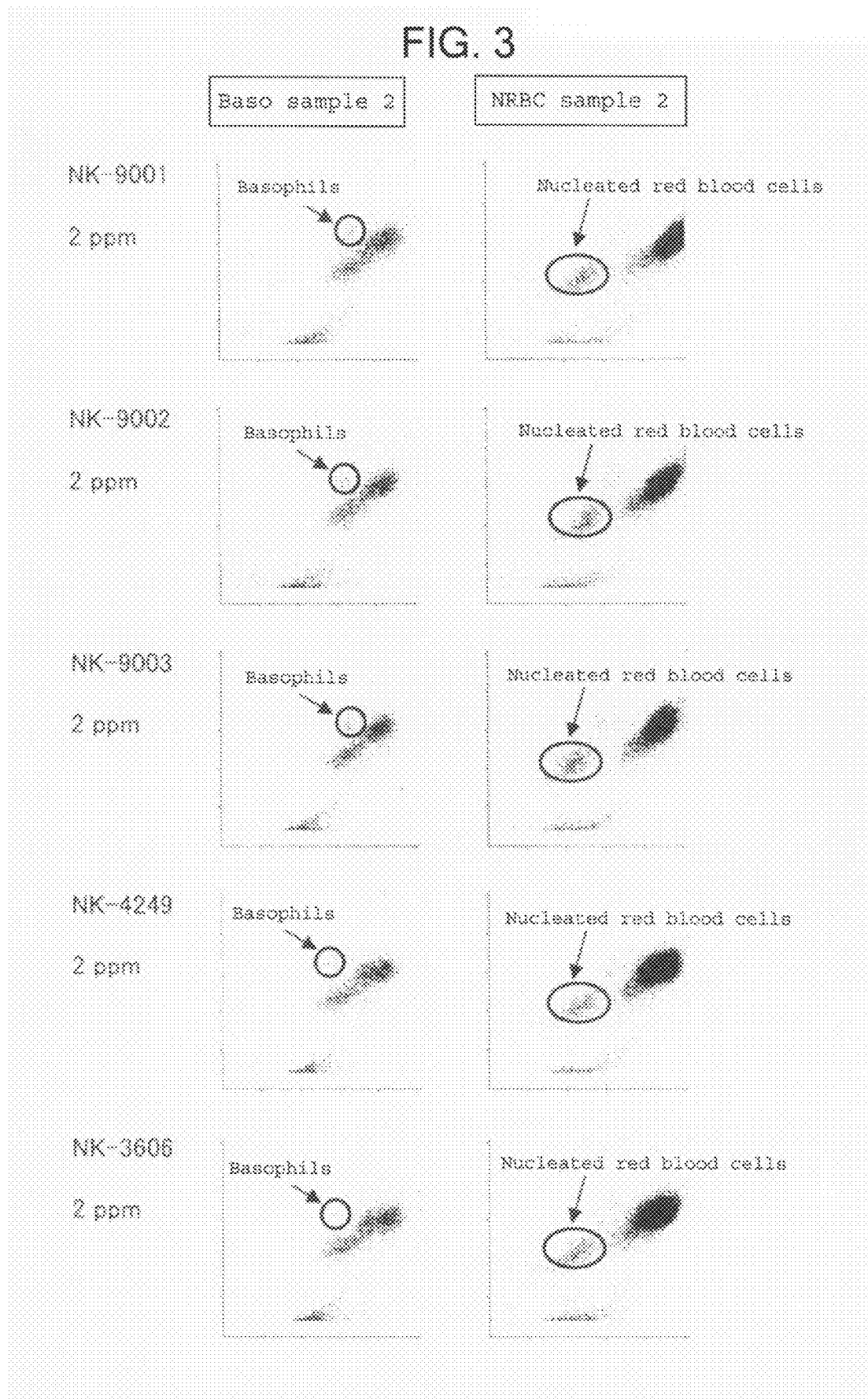

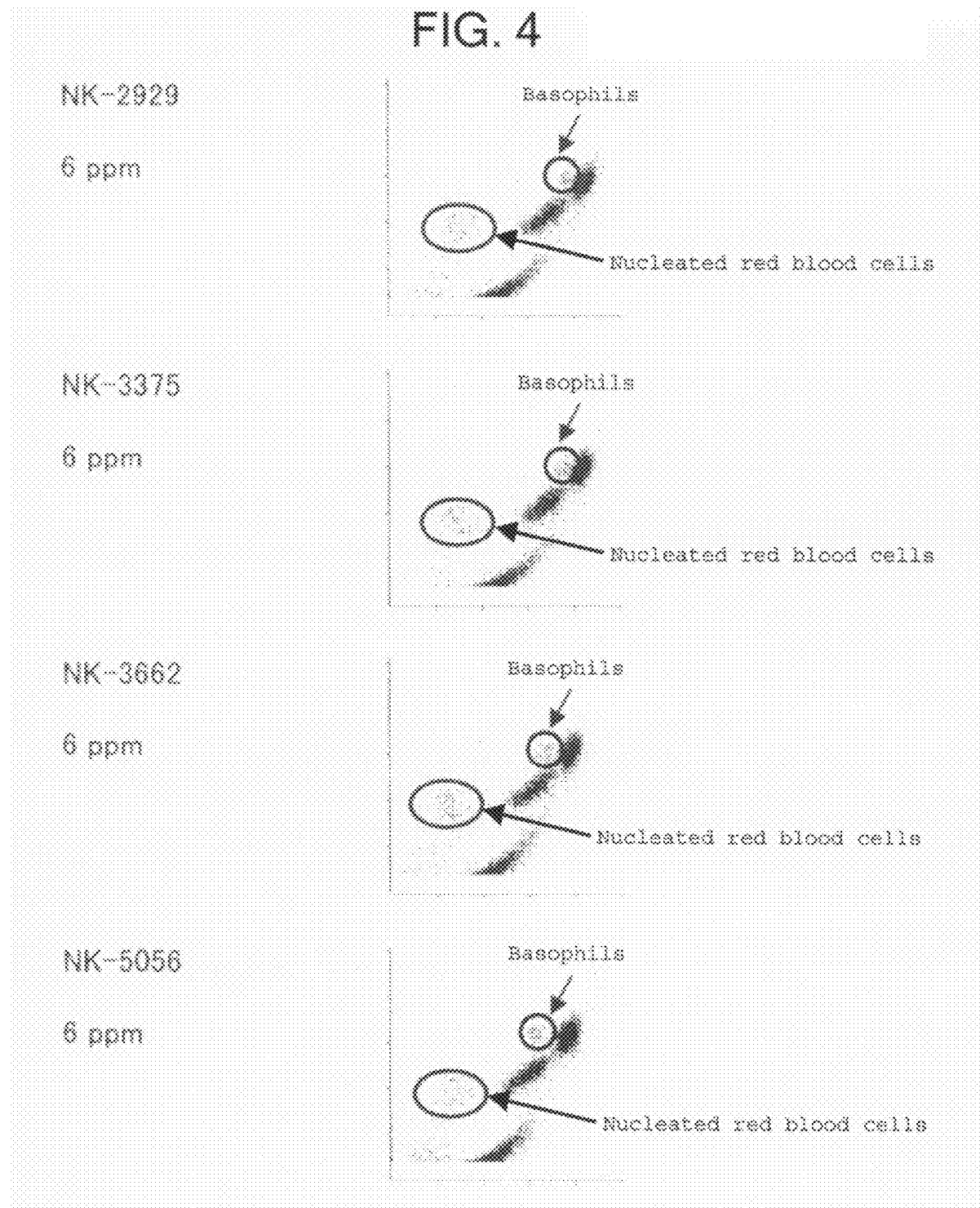

REAGENT FOR SAMPLE ANALYSIS, KIT FOR SAMPLE ANALYSIS AND METHOD FOR SAMPLE ANALYSIS

FIELD OF THE INVENTION

The present invention relates to a reagent for sample analysis for analyzing hemocytes in a sample collected from a living body, a kit for sample analysis and a method for sample analysis.

BACKGROUND

In the field of a clinical test, analysis of hemocyte components in a sample is very useful for diagnosing a variety of diseases in a circulatory organ of a subject. Depending on a disease, the number of particular hemocytes is increased or decreased, or blood cells which are not usually present appear in peripheral blood in some cases.

In recent years, various automatic hemocyte counting devices, to which a principle of flow cytometry is applied, are commercially available. Using such devices, sorting and counting of hemocyte cells are performed in general laboratories. When these automatic hemocyte counting devices are used, sorting and counting of leukocytes in a sample can be automatically performed.

For sorting and counting leukocytes, first, erythrocytes in a blood sample are lyzed. When the resulting sample is guided to a detector, and an electric impedance signal is detected, leukocytes can be sorted into three kinds. Alternatively, by the following method, leukocytes can be sorted into five kinds; lymphocytes, monocytes, neutrophils, eosinophils, and basophils. First, erythrocytes in a blood sample are lyzed, and hemocytes in the resulting sample are stained with a fluorescent dye. Then, hemocytes are irradiated with excited light, and a fluorescent signal and a scattered light signal emitted from the hemocytes are detected. By analyzing those signals, leukocytes can be sorted into five kinds.

Since the number of basophils is usually small, only basophils may be measured without sorting leukocytes into five kinds by one measurement. Based on the property that basophils are hardly destroyed under acidic conditions as compared with other leukocytes, the number of basophils can be determined by treating a blood sample exclusively for measurement of basophils (see Japanese Examined Patent Publication (JP-B) No. 6-8817). When this result and the result of leukocyte sorting obtained by another method are combined, leukocytes can be sorted into five kinds more correctly.

Appearance of nucleated red blood cells (NRBC) often becomes a problem in leukocyte measurement. Since nucleated red blood cells have a nucleus, a nucleus remains even when erythrocytes are lyzing-treated. Since the remaining nucleus emits a signal similar to that of lymphocytes in the aforementioned measuring method, a plus error is generated at the time of measurement of the number of leukocytes. In order to exclude this influence, for example, there is a method of performing a treatment exclusive for measurement of nucleated red blood cells, and determining the number of nucleated red blood cells (Japanese Unexamined Patent Publication (JP-A) No. 10-339729), and subtracting the number of nucleated red blood cells from the number of leukocytes obtained by another method. By this method, the correct number of leukocytes can be obtained.

However, when a treatment exclusive for particular hemocytes is increased in order to correctly sort leukocytes, this is troublesome, and there is a possibility that a device is complicated, or scaled up. In addition, when a plurality of reagents exclusive for particular hemocytes are used, the cost of a total blood test is increased. From such a point of view, it is preferable that a treatment exclusive for particular hemocyte is performed as little as possible.

Measurement of basophils and nucleated red blood cells can be performed by treating a blood sample under acidic condition. Therefore, when a blood sample is treated under acidic condition, there is a possibility that both of basophils and nucleated red blood cells can be measured by one measurement. For example, JP-A No. 2002-148261 discloses a method of measuring basophils and erythroblasts (nucleated red blood cells) comprising mixing an aqueous solution containing an erythrocyte lyzing agent and a surfactant which bring leukocytes and abnormal cells into a state suitable for staining, with a sample, adding a dyeing solution containing a fluorescent dye to stain it, and measuring a fluorescent intensity and a scattered light intensity with a flow cytometer.

However, in the case of a specimen containing many leukocytes, the aforementioned conventional method does not sufficiently separate basophils and leukocytes other than basophils in some cases.

SUMMARY

The scope of the present invention is defined solely by the appended claims, and is not affected to any degree by the statements within this summary.

A first aspect of the present invention is a reagent for sample analysis for measuring basophils and/or nucleated red blood cells, comprising at least one kind of fluorescent dye selected from a fluorescent dye of the general formula (I):

[Chemical formula 1]

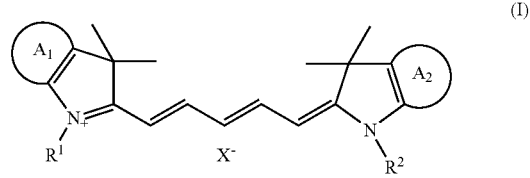

(wherein $R^1$ and $R^2$ are identical or different and each represents an alkyl group;

[Chemical formula 2]

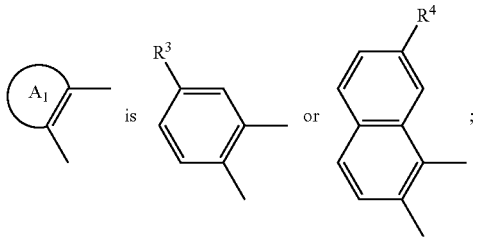

provided that when

[Chemical formula 3]

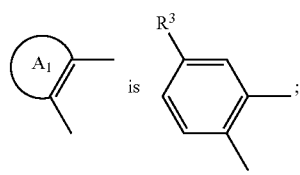

and when

[Chemical formula 4]

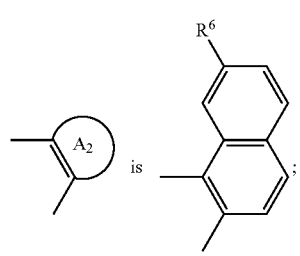

[Chemical formula 5]

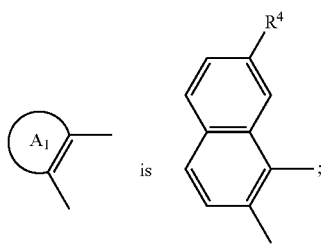

and when

[Chemical formula 6]

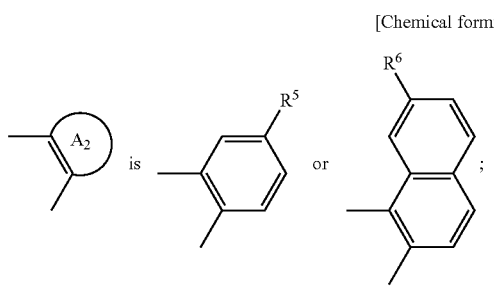

$R^3$, $R^4$, $R^5$ and $R^6$ are identical or different and each represents a hydrogen atom or an alkyl group; and
$X^-$ represents an anion)
and a fluorescent dye of the general formula (II):

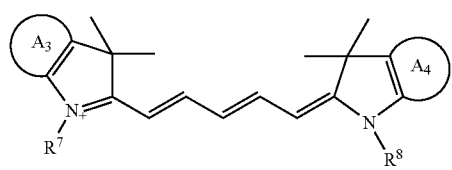
(II)

(wherein $R^7$ and $R^8$ are identical or different and each represents an alkyl group optionally having an acidic group;

[Chemical Formula 8]

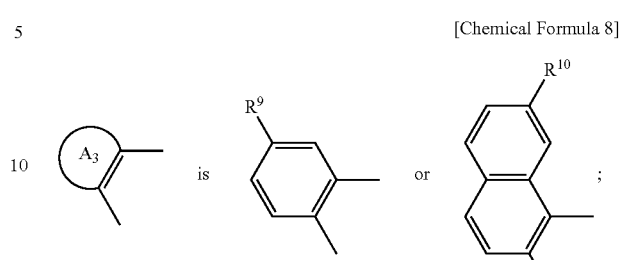

[Chemical Formula 9]

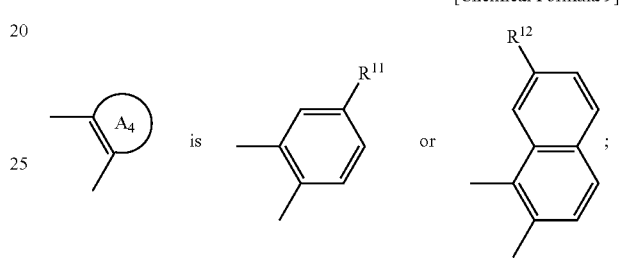

$R^9$, $R^{10}$, $R^{11}$ and $R^{12}$ are identical or different and each represents a hydrogen atom or an acidic group,
provided that any one of $R^7$ to $R^{12}$ has an acidic group;
an acidic group which may be present on $R^7$ to $R^{12}$ may form a salt, provided that any one of acidic groups which can be present on $R^7$ to $R^{12}$ is a group which has released a proton).

A second aspect of the present invention is a kit for measuring basophils and/or nucleated red blood cells, comprising a solution containing a surfactant which lyzes erythrocytes, and imparts damage to a cell membrane of leukocytes to such an extent that a fluorescent dye can permeate therethrough, and a solution containing at least one kind of fluorescent dye selected from the fluorescent dye of the general formula (I) and the fluorescent dye of the general formula (II).

Further, a third aspect of the present invention is a method for sample analysis, comprising a step of staining hemocytes in a sample with at least one kind of fluorescent dye of the fluorescent dye of the general formula (I) and the fluorescent dye of the general formula (II); a step of irradiating the stained hemocytes with light, and obtaining scattered light information and fluorescent information; and a step of discriminating and/or counting basophils and/or nucleated red blood cells in the sample based on the scattered light information and the fluorescent information.

BRIEF DESCRIPTION OF THE DRAWINGS

FIG. 2 shows a schematic view of a scattergram used when a sample is analyzed using the reagent for sample analysis of the present invention (Example 1).

FIG. 3 shows a schematic view of a scattergram used when a sample is analyzed using the reagent for sample analysis of the present invention (Example 1).

FIG. 4 shows a schematic view of a scattergram used when a sample is analyzed using the reagent for sample analysis of the present invention (Example 2).

DETAILED DESCRIPTION OF THE PREFERRED EMBODIMENTS

Figure 1:
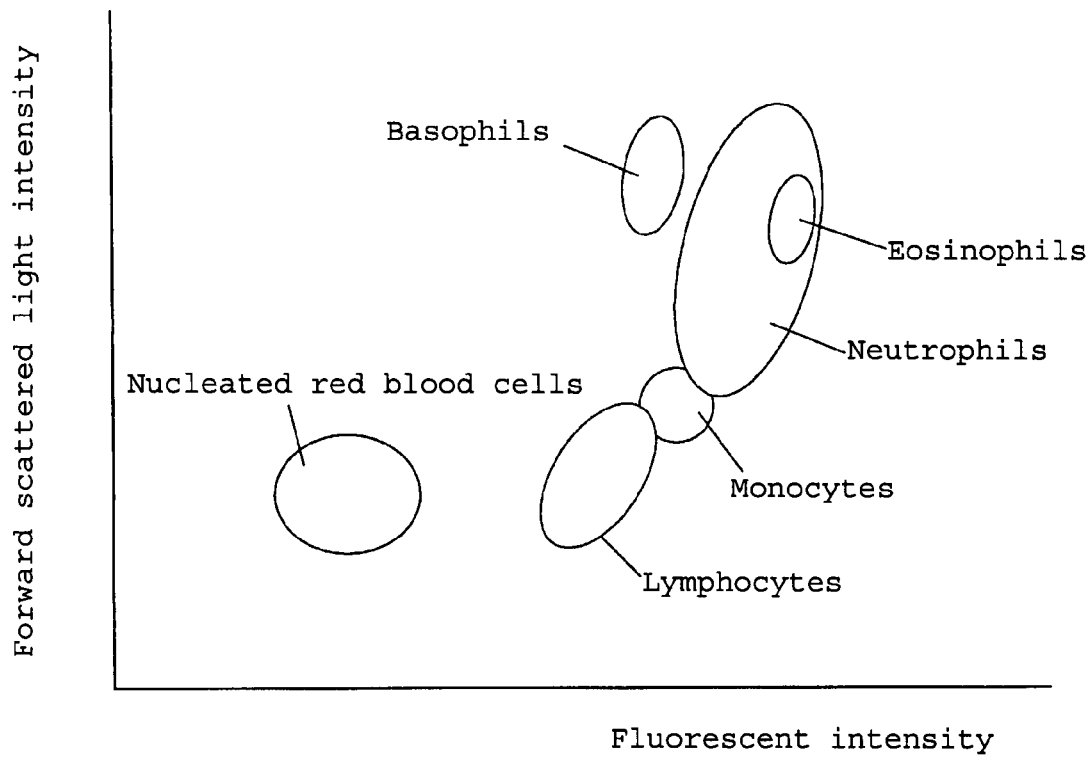
FIG. 1 shows a schematic view of a scattergram used when a sample is analyzed using the reagent for sample analysis of the present invention.

The preferred embodiments of the present invention are described hereinafter with reference to the drawings.

Basophils which can be measured by the present invention are a kind of leukocytes which are stained with a basic dye, and have large acidic granules. And, nucleated red blood cells are generally also called erythroblasts, and include proerythroblasts, basophilic erythroblasts, polychromatic erythroblasts and orthochromatic erythroblasts.

As used herein, the "sample" refers to a body fluid sample such as blood, marrow fluid, urine, and a sample collected by apheresis, which are taken from a mammal, preferably a human.

The fluorescent dye contained in the reagent of the present invention is represented by the general formula (I) and/or (II).

As used herein, the "alkyl group" in the general formulas (I) and (II) may be straight or branched. The number of carbon atoms of the alkyl group is usually 1 to 20, preferably 1 to 10 and, from a viewpoint of solubility in water of the fluorescent dye, the carbon number is more preferably 1 to 6. Preferable examples of the alkyl group include methyl, ethyl, propyl, butyl, pentyl and hexyl.

Examples of the anion $X^-$ in the general formula (I) include halogen ions such as $F^-$, $Cl^-$, $Br$ and $I^-$, $CF_3SO_3^-$, $BF_4^-$, and $ClO_4^-$.

As used herein, the "acidic group" which can be present in the general formula (II) includes both a group which can release a proton, and an acid group in which a group which can release a proton has released a proton. Examples of the group which can release a proton include a carboxyl group, a sulfonic acid group, and a phosphoric acid group. A carboxyl group or a sulfonic acid group is preferable.

The acidic group may form a salt. Examples of such salt include alkali metal salts such as a sodium salt and a potassium salt, an ammonium salt, and alkylammonium salts such as a triethylammonium salt. A preferable salt is an alkali metal salt or an alkylammonium salt, and a more preferable salt is a sodium salt or a triethylammonium salt.

One or two or more kinds of fluorescent dyes of the general formulas (I) and (II) can be used.

The aforementioned fluorescent dye can be purchased, for example, from Hayashibara biochemical laboratories, Inc.

A concentration of the dye in the reagent of the present invention can be appropriately selected depending on the kind of the dye, and is generally 0.01 to 100 mg/L, preferably 0.1 to 10 mg/L, more preferably 0.3 to 6.0 mg/L.

Since the fluorescent dye of the general formula (I) and the general formula (II) contained in the reagent for sample analysis of the present invention has stronger affinity for eosinophils and neutrophils than affinity for basophils, it stains eosinophils and neutrophils stronger as compared with basophils. Using these fluorescent dyes, basophils among granulocytes can be clearly discriminated based on a difference in fluorescence emitted from stained cells. In addition, basophils can be clearly distinguished also from lymphocytes and monocytes based on a difference in a size of cells and a structure of subcellular organelles.

Upon staining of hemocytes with the reagent for sample analysis of the present invention, it is preferable that erythrocytes, which become an obstacle for measuring nucleated red blood cells and leukocytes (lymphocytes, monocytes, neutrophils, eosinophils, basophils), are hemolyzed, thereby, imparting damage to a cell membrane of nucleated red blood cells and leukocytes. By this damage, permeability of the fluorescent dye into nucleated red blood cells and leukocytes is improved, and hemocytes can be effectively stained.

Usually, a pore is generated on a cell membrane of erythrocytes at an osmotic pressure of not greater than about 150 mOsm/kg. When hemoglobin in the interior of erythrocytes is eluted through the pore, erythrocytes become optically transparent (hemolysis). Erythrocytes which have become optically transparent do not substantially become an obstacle for measurement using flow cytometry. For hemolyzing erythrocytes, low osmotic pressure conditions and low pH conditions are preferable. An osmotic pressure satisfying these two conditions is 20 mOsm/kg to 150 mOsm/kg.

The pH of the reagent of the present invention is preferably 2.0 to 4.5, more preferably 2.0 to 3.5. When the pH is within this range, granules of basophils are stabilized. In addition, erythrocytes can be effectively hemolyzed without imparting excess influence on leukocytes and nucleated red blood cells. When a sample is treated at this pH, scattered light and fluorescence of non-nucleated erythrocytes become extremely small, and do not substantially adversely influence on measurement of nucleated red blood cells and leukocytes.

The pH of the reagent may be adjusted using a buffer. A preferable buffer is a buffer having pKa around a desired pH ±2.0. For example, citric acid, malic acid, diglycol acid, malonic acid, and maleic acid can be used as a buffer.

The concentration of the buffer in the reagent of the present invention is not particularly limited as far as it can retain the pH in the aforementioned range.

In order that an osmotic pressure of the reagent of the present invention is in an appropriate range for hemolysis of erythrocytes, for example, an electrolyte such as NaCl and KCl, and sugars can be used. Alternatively, an osmotic pressure can be adjusted with the concentration of the buffer.

It is preferable that the reagent of the present invention contains a surfactant hemolyzing erythrocytes and imparting damage to a cell membrane of leukocytes to such an extent that a fluorescent dye can permeate therethrough. It is preferable to use a cationic surfactant as the surfactant. More preferable is a quaternary ammonium salt or a pyridinium salt. It is preferable to use, as the quaternary ammonium salt, for example, a quaternary ammonium salt represented by the following formula:

[Chemical formula 10]

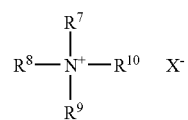

(wherein $R^7$, $R^8$ and $R^9$ are identical or different and each represents a hydrogen atom, a $C_{1-8}$alkyl group or a $C_{6-8}$aralkyl group; $R^{10}$ is a $C_{8-18}$alkyl group, a $C_{8-18}$alkenyl group or a $C_{6-18}$aralkyl group; $X^-$ represents an anion). It is preferable to use, as the pyridinium salt, for example, a pyridinium salt represented by the following formula:

[Chemical formula 11]

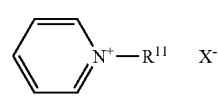

(wherein $R^{11}$ is a $C_{8-18}$alkyl group; $X^-$ represents an anion)

Such surfactant is known and, for example, surfactants disclosed in JP-A No. 2002-148261 can be used.

Examples of the surfactant include decyltrimethylammonium bromide, dodecyltrimethylammonium chloride, octyltrimethylammonium bromide, octyltrimethylammonium chloride, lauryltrimethylammonium bromide, lauryltrimethylammonium chloride, myristyltrimethylammonium bromide, myristyltrimethylammonium chloride and laurylpyridinium chloride.

The concentration of the surfactant in the reagent of the present invention is preferably 10 to 10000 mg/l, more preferably 100 to 5000 mg/l. At a concentration within this range, erythrocytes can be effectively hemolyzed without imparting excess influence on leukocytes and nucleated red blood cells.

It is preferable that the reagent of the present invention contains at least one kind of organic acid having at least one aromatic ring in a molecule (hereinafter, referred to as "aromatic organic acid") or a salt thereof. By using the aromatic organic acid, erythrocytes can be hemolyzed more effectively in a short time. A preferable aromatic organic acid is salicylic acid or phthalic acid.

The concentration of the aromatic organic acid or a salt thereof in the reagent for sample analysis of the present invention is not particularly limited as far as the pH of the reagent of the present invention is in the aforementioned range, but is preferably 0.1 to 100 mM, more preferably 1 to 50 mM.

The reagent of the present invention can be obtained by dissolving the fluorescent dye and, as desired, the surfactant and the aromatic organic acid or a salt thereof in an appropriate solvent to the aforementioned concentration and, as desired, adjusting the pH using NaOH or HCl. Alternatively, the reagent can also be obtained by mixing a solution of the fluorescent dye and, as desired, a solution of the surfactant and a solution of the aromatic organic acid or a salt thereof, dissolved in an appropriate solvent, respectively, so that final concentrations of these respective components are in the aforementioned ranges and, as desired, adjusting the pH using NaOH or HCl. The appropriate solvent is not particularly limited as far as it can dissolve the components, but examples include water, alcohol, ethylene glycol, dimethyl sulfoxide (DMSO), and a mixture thereof.

It is preferable to mix the reagent of the present invention with a sample in such an amount that a volume ratio of the reagent: sample is 5 to 1000:1, more preferably 10 to 500:1. By mixing the reagent and the sample in such a ratio, lysis of erythrocytes progresses rapidly, thereby, staining of hemocyte components can be performed well. In addition, when the amount of the sample is around a few μl to 100 μl, measurement can be performed well.

A kit comprising a first reagent containing the surfactant and a second reagent containing the fluorescent dye is one of the present invention. The first reagent and the second reagent are a solution containing the surfactant and a solution containing the fluorescent dye, respectively. A solvent used in these solutions is not particularly limited as far as it can dissolve the surfactant or the fluorescent dye. For example, water, an alcohol, an organic solvent (ethylene glycol, dimethyl sulfoxide (DMSO) etc.), and a mixture thereof can be used as the solvent. When a fluorescent dye having low long-term storage stability in an aqueous solution is used, it is preferable to dissolve the material in the organic solvent.

The first reagent may contain the aromatic organic acid or a salt thereof.

Alternatively, the kit of the present invention may further contain a third reagent containing an aromatic organic acid or a salt thereof apart from the first reagent and the second reagent.

The method for sample analysis of the present invention comprises a step of staining hemocytes in a sample with the fluorescent dye, a step of irradiating the stained hemocytes with light, and obtaining scattered light information and fluorescent information, and a step of separating basophils in a sample from other leukocyte components, and counting basophils based on the obtained scattered light information and fluorescent information. It is preferable that, in the staining step, erythrocytes are hemolyzed, damage is imparted to a cell membrane of hemocytes other than hemolyzed erythrocytes to such an extent that the fluorescent dye can permeate therethrough, and damaged hemocytes are stained.

In the staining step, the fluorescent dye and the sample are mixed. In this step, preferably, the fluorescent dye, the surfactant and the sample are mixed. Since this surfactant imparts damage to a cell membrane of hemocytes to such an extent that the fluorescent dye can permeate therethrough, it becomes possible to effectively stain hemocytes to be measured with the fluorescent dye, by mixing the surfactant and the sample.

When the surfactant is used in the staining step, an order of mixing the surfactant, the fluorescent dye and the sample is not particularly limited. The surfactant and the fluorescent dye may be mixed in advance, and the mixture and the sample may be mixed. Alternatively, the surfactant and the sample may be mixed in advance, and the mixture and the fluorescent dye maybe mixed. Irrespective of the mixing order, equivalent measuring result can be obtained.

In the staining step, the reagent of the present invention and the sample may be mixed. Alternatively, each constituent component of the reagent kit of the present invention may be mixed with the sample.

In the staining step, it is preferable that, after the fluorescent dye and the sample are mixed, they are reacted at a temperature of 15 to 50° C., preferably 20 to 40° C. for 5 to 120 seconds, preferably for 5 to 30 seconds.

Hemocytes stained in the staining step may be analyzed using a flow cytometer. Analysis of hemocytes using the flow cytometer will be explained below. By irradiating hemocytes with light when stained hemocytes pass through a flow cell of the flow cytometer, scattered light information and fluorescent information can be obtained. Scattered light information is not particularly limited as far as the light is scattered light which can be measured with a commercially available general flow cytometer. For example, a scattered light width and a scattered light intensity of scattered light such as forward scattered light (e.g. light receiving angle around 0 to 20 degrees) and side scattered light (light receiving angle around 90 degrees) can be used as scattered light information. Generally, it is known that side scattered light reflects internal information of a nucleus and granules of a cell, and forward scattered light reflects information of a size of a cell. It is preferable that, in the method of the present invention, a forward scattered light intensity is used as scattered light information.

Fluorescent information is obtained by irradiating a measurement sample with light having an appropriate wavelength, and measuring excited fluorescence. An appropriate light receiving wavelength can be selected depending on the fluorescent dye used. Fluorescence is emitted from a nucleic acid and granules in a cell stained with the fluorescent dye.

The light source for the flow cytometer used is not particularly limited, but a light source of an appropriate wavelength for exciting the fluorescent dye is selected. For example, a red semiconductor laser, a blue semiconductor laser, an argon laser, and a He—Ne laser are used. Particularly, a semiconductor laser is very inexpensive as compared with a gas laser, being preferable.

Based on scattered light and fluorescence measured as described above, nucleated red blood cells and basophils can be counted by discriminating from other components. It is preferable that this step includes (1) producing a scattergram using fluorescent information and forward scattered light information as two axes, and (2) analyzing the resulting scattergram with an appropriate analysis software. When the scattergram is drawn taking a fluorescent intensity on an X axis and a forward scattered light intensity on a Y axis, for example, as shown in FIG. 1, each cell is distributed, forming a population (cluster). Nucleated red blood cells have a smaller size than that of granulocytes (neutrophils, eosinophils and basophils). Therefore, in such a scattergram, nucleated red blood cells appear in a region where a forward scattered light intensity is smaller than that of granulocytes, and a fluorescent intensity is smaller than that of leukocytes. This can clearly discriminate leukocytes and nucleated red blood cells. And, basophils appear in a region where a fluorescent intensity is smaller than that of eosinophils or neutrophils. This can clearly discriminate basophils from other granulocytes. In addition, to which hemocyte each population on the scattergram corresponds can be specified by treating a sample containing only each hemocyte with the reagent of the present invention and, thereafter, performing measurement to confirm an appearance position.

By analyzing a population on the scattergram with an appropriate analysis software, the numbers and a ratio of nucleated red blood cells and basophils can be calculated. Specifically, when a cell population is recognized at a position where a prescribed cell is thought to appear in the scattergram, a center of this population is first specified. Between this center and an appearance region of another cell population, up to a part where a cell of a prescribed cell population appears can be set as a boundary of this cell population. A cell appearing in a set region can be counted as a prescribed cell. In addition, by counting leukocytes other than basophils, a ratio of basophils relative to total leukocytes (basophils/total leukocytes: hereinafter, referred to as "basophile ratio"), and a ratio of nucleated red blood cells relative to total leukocytes (nucleated red blood cells/total leukocytes: hereinafter, referred to as "nucleated red blood cell ratio") can be calculated. The nucleated red blood cell ratio is expressed usually as a percentage of nucleated red blood cells appearing per 100 leukocytes, and a unit is represented as "cells/100 WBC".

When the reagent for sample analysis, the kit for sample analysis and the method for sample analysis of the present invention are used, a population formed by nucleated red blood cells, and a population formed by basophils are clearly separated from a population formed by other hemocyte cells, respectively. For this reason, more precise sorting and/or counting of the number of leukocytes can be performed.

The present invention will be explained in more detail by way of the following Examples, but various variations and modifications are possible to the present invention, and the scope of the present invention is not limited by the following Examples.

EXAMPLES

Fluorescent dyes used in the following Examples are as follows.

[Chemical formula 12]

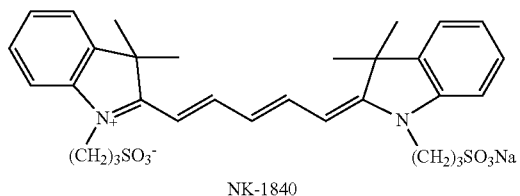

NK-1840

[Chemical formula 13]

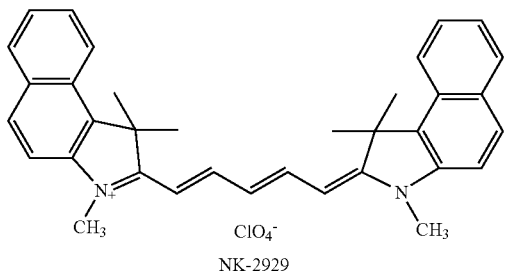

NK-2929

[Chemical formula 14]

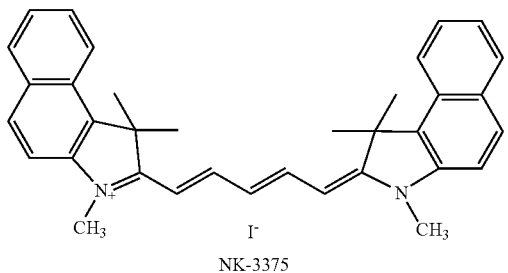

NK-3375

[Chemical formula 15]

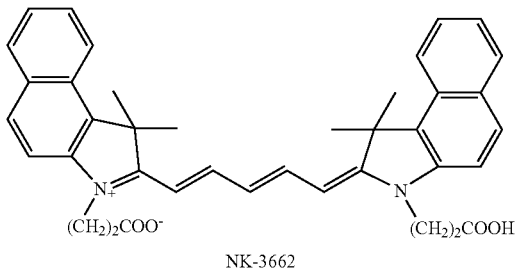

NK-3662

[Chemical formula 16]

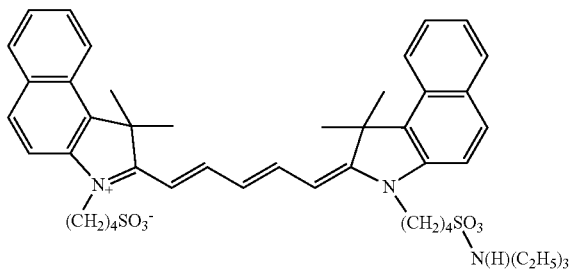

NK-5056

[Chemical formula 17]

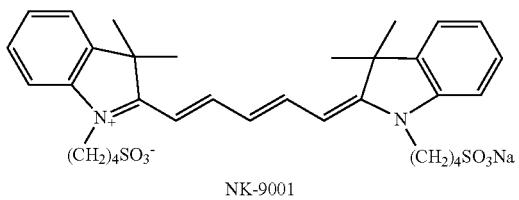

NK-9001

-continued

[Chemical formula 18]

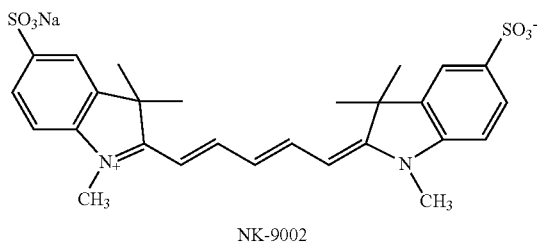

NK-9002

[Chemical formula 19]

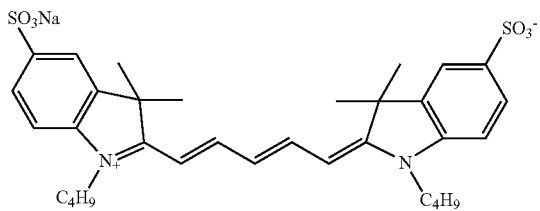

NK-9003

[Chemical formula 20]

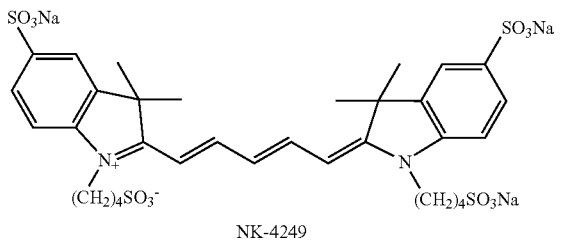

NK-4249

[Chemical formula 21]

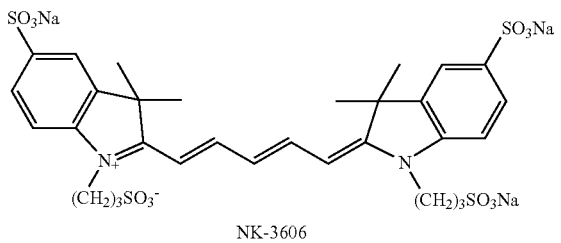

NK-3606

[Chemical formula 22]

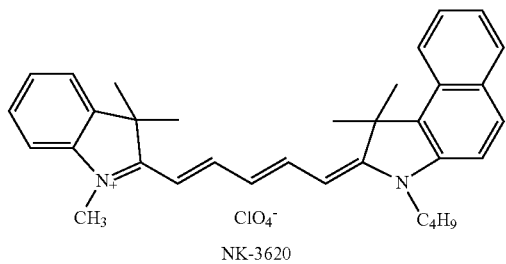

NK-3620

Comparative Example 1

Blood collected from each of two subjects was used as a sample. Basophils contained in two specimens of a blood sample were measured using an automatic hemocyte counting device XE-2100 (manufactured by Sysmex Corporation: loaded with a red semiconductor laser (633 nm)), and a basophile ratio was calculated. As a reagent, STROMATO-LYZER-FB (II) (manufactured by Sysmex Corporation) was used.

As a result of measurement, it was recognized that these samples have a high content of basophils (hereinafter, these samples are referred to as Baso sample 1 and Baso sample 2). The basophile ratio of the Baso sample 1 was 2.3%, and the basophile ratio of the Baso sample 2 was 1.7%. These results served as a control for Example 1.

Then, blood collected from each of two subjects other than the above was used as a sample. Nucleated red blood cells contained in two specimens of the blood sample were measured using an automatic hemocyte counting device XE-2100, and a nucleated red blood cell ratio was calculated. As a reagent, STROMATOLYZER-NR (manufactured by Sysmex Corporation) was used.

As a result of measurement, it was recognized that nucleated red blood cells appear in these samples (hereinafter, these samples are referred to as NRBC sample 1 and NRBC sample 2). The nucleated red blood cell ratio of the NRBC sample 1 was 3.0/100 WBC, and a nucleated red blood cell ratio of the NRBC sample 2 was 5.9/100WBC. These results served as a control for Example 1.

Example 1

Into a constant temperature bath at 35° C. was placed 1 mL of an aqueous solution containing 10 mM salicylic acid (pH: 3.0) and 3000 ppm of decyltrimethylammonium bromide (DTAB). Each dye described in FIGS. 2 and 3 (NK-1840 2 ppm, NK-2929 6 ppm, NK-3375 6 ppm, NK-3662 6 ppm, NK-5056 6 ppm, NK-3620 6 ppm, NK-9001 2 ppm, NK-9002 2 ppm, NK-9003 2 ppm, NK-4249 2 ppm, and NK-3606 2 ppm) was added thereto to the aforementioned concentration, respectively, to dissolve it, thereby, a reagent for sample analysis was obtained.

1 mL of the resulting reagent was sufficiently mixed with 20 μm of a blood sample (Baso sample 1 or 2, or NRBC sample 1 or 2). After a reaction at 35° C. for 20 seconds, the sample was taken out from the constant temperature bath, and was guided to a detection part of a flow cytometer having an excitation light source of 633 nm. Cells in the sample were irradiated with excited light, and a scattered light signal and a fluorescence signal emitted from the cells were detected. The resulting signals were analyzed to determine basophils, nucleated red blood cells and total leukocytes in the sample. This determination was performed using an automatic hemocyte counting device XE-2100.

Determination was performed by adding a reagent containing NK1840, a reagent containing NK2929, a reagent containing NK3375, a reagent containing NK3662, a reagent containing NK5056, and a reagent containing NK3620, respectively, to the Baso sample 1.

Determination was performed by adding a reagent containing NK9001, a reagent containing NK9002, a reagent containing NK9003, a reagent containing NK4249, and a reagent containing NK3606, respectively, to the Baso sample 2.

Determination was performed by adding a reagent containing NK1840, a reagent containing NK2929, a reagent containing NK3375, a reagent containing NK3662, a reagent containing NK5056, and a reagent containing NK3620, respectively, to the NRBC sample 1.

Determination was performed by adding a reagent containing NK9001, a reagent containing NK9002, a reagent containing NK9003, a reagent containing NK4249, and a reagent containing NK3606, respectively, to the NRBC sample 2.

Regarding each sample, a scattergram using a fluorescent intensity and a forward scattered light intensity as two axes was produced. This scattergram is shown in FIG. 2 and FIG. 3. Based on this scattergram, total leukocytes, basophils and nucleated red blood cells were counted, and a basophile ratio and a nucleated red blood cell ratio were calculated. The basophile ratios in the Baso samples calculated in Comparative Example 1 and the present Example are shown in Table 1, and the nucleated red blood cell ratios in the NRBC samples are shown in Table 2.

TABLE 1

| | | Basophil ratio (%) | |
|---|---|---|---|
| Sample | Dye added to reagent | Example 1 | Comparative Example 1 |
| Baso sample 1 | NK-1840 | 2.0 | 2.3 |
| | NK-2929 | 1.7 | |
| | NK-3375 | 1.8 | |
| | NK-3662 | 2.1 | |
| | NK-5056 | 2.0 | |
| | NK-3620 | 1.9 | |
| Baso sample 2 | NK-9001 | 1.7 | 1.7 |
| | NK-9002 | 1.8 | |
| | NK-9003 | 1.9 | |
| | NK-4249 | 2.2 | |
| | NK-3606 | 1.5 | |

TABLE 2

| | | Nucleated red blood cell ratio (cells/100 WBC) | |
|---|---|---|---|
| Sample | Dye added to reagent | Example 1 | Comparative Example 1 |
| NRBC sample 1 | NK-1840 | 4.0 | 3.0 |
| | NK-2929 | 3.7 | |
| | NK-3375 | 4.7 | |
| | NK-3662 | 5.4 | |
| | NK-5056 | 3.7 | |
| | NK-3620 | 4.7 | |
| NRBC sample 2 | NK-9001 | 5.3 | 5.9 |
| | NK-9002 | 5.3 | |
| | NK-9003 | 5.7 | |
| | NK-4249 | 4.9 | |
| | NK-3606 | 5.2 | |

As shown in FIGS. 2 and 3, it is seen that, when the reagent for sample analysis of the present invention is used, basophils are clearly fractionated from leukocyte components other than basophiles, and nucleated red blood cells are also clearly fractionated. Like this, as shown in FIGS. 2 and 3, cells appearing in a constant region on the scattergram were specified as basophils and nucleated red blood cells, and the numbers of them and ratios relative to total leukocyte number were obtained.

In addition, from Tables 1 and 2, a ratio calculated in Example 1 was a value approximate to a ratio calculated in Comparative Example 1. Therefore, it was confirmed that, when the reagent for sample analysis of the present invention is used, nucleated red blood cells and basophils can be determined at almost the same precision as that when nucleated red blood cells and basophils are measured using separate reagents, respectively.

Comparative Example 2

In the same manner as that of Comparative Example 1 except that a sample having a high content of basophils and in which nucleated red blood cells appeared (hereinafter, referred to as BN sample) was used in place of the sample used in Comparative Example 1, basophils in the sample were determined, and a basophile ratio was calculated. The basophile ratio was 2.1%. In addition, apart from determination of basophils, nucleated red blood cells were also determined using the BN sample, and a nucleated red blood cell ratio was calculated. The nucleated red blood cell ratio was 3.6 cells/100 WBC. These results served as a control of Example 2. For determining basophils, STROMATOLYZER-FB (II) (manufactured by Sysmex Corporation) was used as a reagent, and an automatic hemocyte counting device XE-2100 (manufactured by Sysmex Corporation) was used as a device. For determining nucleated red blood cells, STROMATOLYZER-NR (manufactured by Sysmex Corporation) was used as a reagent, and an automatic hemocyte counting device XE-2100 (manufactured by Sysmex Corporation) was used as a device.

Example 2

In the same manner as that of Example 1 except that the BN sample was used in place of the sample used in the Example 1 and one of reagents containing NK-2929, NK-3375, NK-3662 and NK-5056 was used as a dye, basophils and nucleated red blood cells were determined, and a basophil ratio and a nucleated red blood cell ratio were calculated. The concentration of the dye in the reagent for sample analysis was adjusted to 6 ppm. These ratios are shown in Table 3. In addition, a scattergram using a forward scattered light intensity and a fluorescent intensity as two axes, produced in the present Example, is shown in FIG. 4.

TABLE 3

| | Basophil ratio (%) | | Nucleated red blood cell ratio (cells/100 WBC) | |
|---|---|---|---|---|
| Dye | Example 2 | Comparative Example 2 | Example 2 | Comparative Example 2 |
| NK-2929 | 1.3 | 2.1 | 3.7 | 3.6 |
| NK-3375 | 1.2 | | 4.1 | |
| NK-3662 | 1.8 | | 3.8 | |
| NK-5056 | 1.9 | | 4.0 | |

From the results of FIG. 4, it was confirmed that, when the reagent for sample analysis of the present invention is used, basophils in a sample can be clearly discriminated from other components, and nucleated red blood cells can be clearly discriminated from other components by one measurement. In addition, from Table 3, a ratio calculated in Example 2 was a value approximate to a ratio calculated in Comparative Example 2. Therefore, it was confirmed that, when the reagent of the present invention is used, nucleated red blood cells and basophils can be determined at almost the same precision as that when nucleated red blood cells and basophils are determined using separate reagents, respectively.

What is claimed is:

1. A reagent kit for measuring basophils and nucleated red blood cells, which comprises
    a solution comprising a cationic surfactant and an aromatic organic acid, wherein the cationic surfactant hemolyzes erythrocytes, and gives damage to a cell membrane of leukocytes to such an extent that a fluorescent dye can permeate therethrough, the cationic surfactant is selected from the group consisting of a quaternary ammonium salt type and a pyridinium salt, and wherein pH of the solution comprising the cationic surfactant is 2.0 to 4.5, and a solution comprising at least one kind of fluorescent dye selected from the group consisting of the following general formulae (I) and (II), the general formula (I):

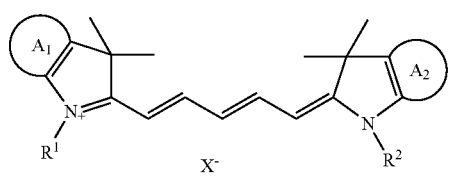

wherein $R^1$ and $R^2$ are identical or different and each represents an alkyl group which has 1-4 carbon atoms;

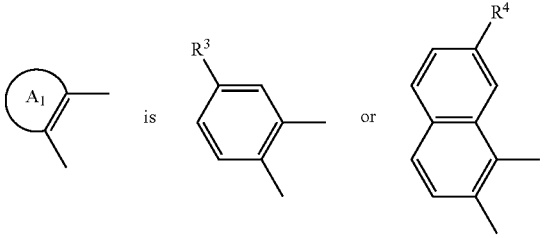

provided that when

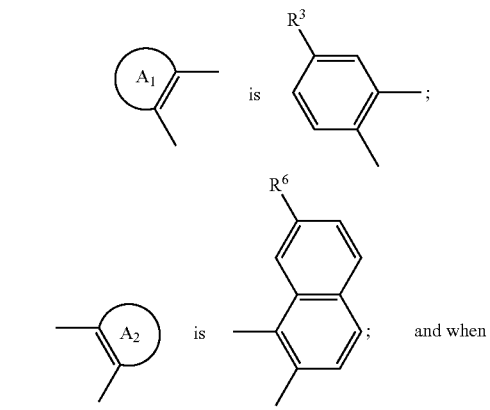

and when

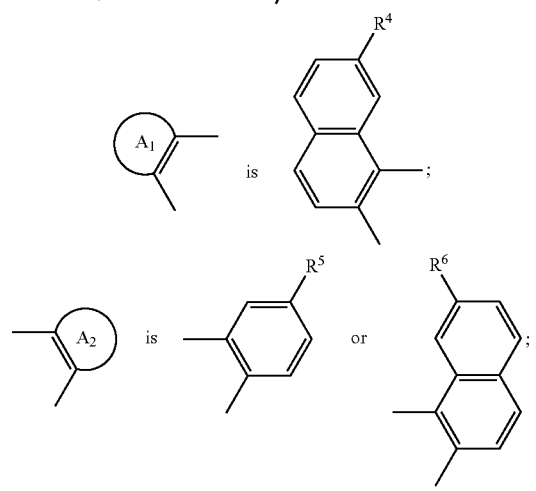

$R^3$, $R^4$, $R^5$ and $R^6$ are identical or different and each represents a hydrogen atom or an alkyl group; and
$X^-$ represents an anion, and
the general formula (II):

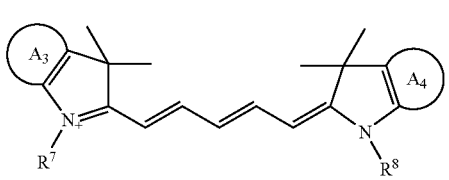

wherein $R^7$ and $R^8$ are identical or different and each represents an alkyl group optionally having an acidic group;

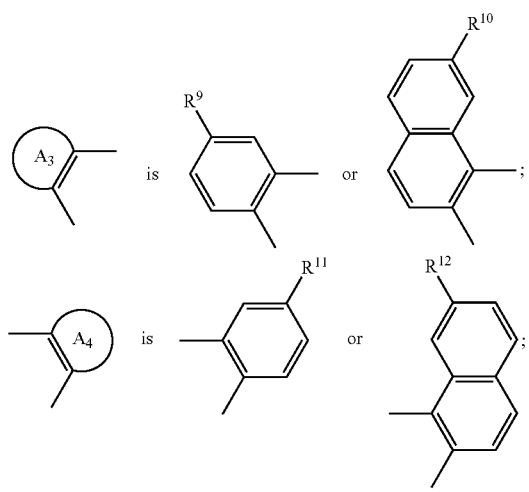

$R^9$, $R^{10}$, $R^{11}$ and $R^{12}$ are identical or different and each represents a hydrogen atom or an acidic group,
provided that any one of $R^7$ to $R^{12}$ has an acidic group;
an acidic group which can be present on $R^7$ to $R^{12}$ may form a salt, provided that any one of acidic groups which can be present on $R^7$ to $R^{12}$ is a group which has released a proton.

2. The kit according to claim 1, wherein the acidic group which can be present on $R^7$ to $R^{12}$ is at least one group selected from the group consisting of a carboxyl group and a sulfonic acid group.

3. The kit according to claim 1, wherein the acidic group which can be present on $R^7$ to $R^{12}$ is at least one group selected from the group consisting of a group forming an alkali metal salt and a group forming an alkylammonium salt.

4. The kit according to claim 1, wherein the aromatic organic acid is at least one of aromatic organic acid selected from the group consisting of salicylic acid, phthalic acid and a salt thereof.

* * * * *